US009593060B2

(12) United States Patent
Enomoto et al.

(10) Patent No.: US 9,593,060 B2
(45) Date of Patent: Mar. 14, 2017

(54) COMPOUNDS FOR ENHANCING GENERATION OF CHEMICAL SPECIES

(71) Applicant: TOYO GOSEI CO., LTD., Inzai-shi (JP)

(72) Inventors: Satoshi Enomoto, Inzai (JP); Yusuke Suga, Inzai (JP)

(73) Assignee: Toyo Gosei CO., LTD, Ichikawa-Shi (JP)

( * ) Notice: Subject to any disclaimer, the term of this patent is extended or adjusted under 35 U.S.C. 154(b) by 0 days.

(21) Appl. No.: 14/547,088

(22) Filed: Nov. 18, 2014

(65) Prior Publication Data

US 2015/0140493 A1   May 21, 2015

Related U.S. Application Data

(60) Provisional application No. 61/905,792, filed on Nov. 18, 2013, provisional application No. 61/906,323, filed on Nov. 19, 2013.

(51) Int. Cl.
| | |
|---|---|
| G03F 7/039 | (2006.01) |
| G03F 7/004 | (2006.01) |
| C07C 43/215 | (2006.01) |
| C07C 69/54 | (2006.01) |
| C07D 317/22 | (2006.01) |

(52) U.S. Cl.
CPC ............ C07C 43/215 (2013.01); C07C 69/54 (2013.01); C07D 317/22 (2013.01); G03F 7/0045 (2013.01); G03F 7/0397 (2013.01)

(58) Field of Classification Search
None
See application file for complete search history.

(56) References Cited

U.S. PATENT DOCUMENTS

| | | | | | |
|---|---|---|---|---|---|
| 4,161,405 | A | * | 7/1979 | Crivello | C08F 2/50 430/280.1 |
| 4,938,790 | A | * | 7/1990 | Smith | C07D 321/12 504/166 |
| 5,162,470 | A | * | 11/1992 | Stenger-Smith | C08G 61/00 526/243 |
| 5,326,661 | A | * | 7/1994 | Sansone | G11B 7/00455 430/20 |
| 5,529,885 | A | * | 6/1996 | Ochiai | G03F 7/0045 430/270.1 |
| 5,535,048 | A | * | 7/1996 | Mignani | C07C 255/37 252/582 |
| 5,665,522 | A | * | 9/1997 | Vogel | G03F 7/105 430/270.1 |
| 5,914,807 | A | | 6/1999 | Downing | |
| 6,267,913 | B1 | * | 7/2001 | Marder | B82Y 10/00 252/301.17 |
| 6,514,434 | B1 | * | 2/2003 | He | C07D 307/52 252/582 |
| 7,335,457 | B2 | * | 2/2008 | Shimizu | G03F 7/0045 430/270.1 |
| 7,851,252 | B2 | | 12/2010 | Nealey et al. | |
| 2005/0214650 | A1 | * | 9/2005 | Takizawa | G03F 7/001 430/1 |
| 2006/0189788 | A1 | * | 8/2006 | Araki | C08F 234/02 528/425 |
| 2008/0050319 | A1 | * | 2/2008 | Koch | A61K 8/35 424/59 |
| 2009/0079913 | A1 | * | 3/2009 | Nishikawa | G02B 5/3083 349/106 |
| 2015/0060728 | A1 | * | 3/2015 | Enomoto | C07C 33/24 252/183.11 |
| 2015/0099893 | A1 | * | 4/2015 | Enomoto | C07C 43/2055 549/26 |
| 2015/0140493 | A1 | | 5/2015 | Enomoto et al. | |
| 2015/0241779 | A1 | * | 8/2015 | Enomoto | G03F 7/0045 430/270.1 |

FOREIGN PATENT DOCUMENTS

| | | | |
|---|---|---|---|
| GB | 1015787 | * | 1/1962 |
| JP | 60-181107 | * | 9/1985 |
| JP | 63-063648 | * | 3/1988 |
| JP | 01-138554 | * | 5/1989 |
| JP | 2004-020735 | * | 1/2004 |
| WO | 2013/091696 | * | 6/2013 |
| WO | 2014185065 A1 | | 11/2014 |
| WO | 2014208076 A1 | | 12/2014 |

(Continued)

OTHER PUBLICATIONS

Singh et al. "Phloroglucinol compounds of natural origin", Nat, Prod., Report., vol. 23 pp. 558-591 (2006).*
Ouyang et al., "Manganese (III) mediated intermolecular cyclization reactions of alkenes and active methylene compounds", J. Heterocyclic Chem., vol. 34 pp. 81-86 (1997).*
Justik etr al., "Oxidative reaarangement of arylalkenens with . . . ", Tetrhed. Lett., vol. 45 pp. 6159-6163 (2004).*
Shin et al., Bull, KR Chem. Soc. (1981), vol. 2(3), pp. 114-121.
Kharchenko et al., Khimiya Geterotsiklicheskikh Soedinenii (1970), vol. 3, pp. 338-341.

(Continued)

Primary Examiner — Martin Angebranndt
(74) Attorney, Agent, or Firm — TraskBritt P.C.

(57) ABSTRACT

A reagent that enhances acid generation of a photoacid generator and composition containing such reagent is disclosed. Also described is a method for manufacturing a device, the method including applying a liquid containing a composition to a member such that a coating film including the composition is formed on the member; and exposing the coating film to at least one of a first electromagnetic ray and a first particle ray such that a first portion of the coating film is exposed to the at least one of the first electromagnetic ray and the first particle ray while a second portion of the coating film is not exposed to the at least one of the first electromagnetic ray and the first particle ray.

3 Claims, 5 Drawing Sheets

(56) References Cited

FOREIGN PATENT DOCUMENTS

| WO | 2014208102 A1 | 12/2014 |
|----|---------------|---------|
| WO | 2014208103 A1 | 12/2014 |
| WO | 2015019616 A1 | 2/2015 |
| WO | 2015022779 A1 | 2/2015 |

OTHER PUBLICATIONS

Office Action for U.S. Appl. No. 14/508,445 dated Dec. 21, 2015.
Office Action for U.S. Appl. No. 14/476,607 dated Jan. 29, 2016.
Photoacid Generator Selection Guide for the electronics industry and energy curable coatings, BASF catalog, 2010, Wyandotte, MI, US.

* cited by examiner (e)

(f)

COMPOUNDS FOR ENHANCING GENERATION OF CHEMICAL SPECIES

CROSS-REFERENCE TO RELATED APPLICATIONS

This application claims the benefit under 35 U.S.C. §119 (e) of U.S. Provisional Patent Application Ser. No. 61/905,792, filed on Nov. 18, 2013, and No. 61/906,323, filed on Nov. 19, 2013, the disclosure of each of which is hereby incorporated herein in its entirety by this reference.

TECHNICAL FIELD

Several aspects of the disclosure relate to the fields of chemistry and material enhancing a generation of a chemical species, such as acid and base. Typical examples of materials relating to an aspect hereof can be used as a constituent of photoresist compositions that can be applied to fabrication of interlayer insulating films of devices such as liquid crystal display (LCD), organic electroluminescent display (OLED), and a semiconductor device.

BACKGROUND

Current high-resolution lithographic processes are based on chemically amplified resists (CARs) and are used to pattern features with fine dimensions.

Methods for forming pattern features with fine dimensions is disclosed in U.S. Pat. No. 7,851,252 (filed on Feb. 17, 2009), the contents of which are incorporated herein by this reference.

BRIEF SUMMARY

A substance relating to an aspect hereof is characterized in that the substance absorbs a light of a wavelength longer than 220 nm; and the substance is capable of sensitizing a compound to enhance a formation of a chemical species from at least one of the substance and the compound. A substance relating to an aspect hereof is characterized in that the substance is capable of donating an energy or an electron to a compound or accepting an energy or an electron from a compound by an exposure of the substance to at least one of a first electromagnetic ray and a first particle ray to enhance a formation of a chemical species from at least one of the substance and the compound.

With regard to the substance, it is preferred that the chemical species is at least one of acid and base.

With regard to the substance, it is preferred that the chemical species is at least one of Brönsted acid and Brönsted base.

With regard to the substance, it is preferred that the substance has a following characteristic: a molar absorption coefficient of the substance at 400 nm when measured in a solution containing the substance is equal to or lower than 200.

With regard to the substance, it is preferred that the substance has a following characteristic: a molar absorption coefficient of the substance at 400 nm when measured in a solution containing the substance is equal to or lower than 100.

With regard to the substance, it is preferred that the substance has a following characteristic: a ratio of an absorbance at 365 nm ("$Ab_{365}$") to an absorbance at 400 nm ("$Ab_{400}$") when measured in a solution containing the substance is equal to or greater than 2.0.

With regard to the substance, it is preferred that the substance has a following characteristic: a ratio of an absorbance at 365 nm ("$Ab_{365}$") to an absorbance at 400 nm ("$Ab_{400}$") when measured in a solution containing the substance is equal to or greater than 50.

With regard to the substance, it is preferred that the substance has a following characteristic: a ratio of an absorbance at 365 nm ("$Ab_{365}$") to an absorbance at 400 nm ("$Ab_{400}$") when measured in a film containing the substance is equal to or greater than 100.

With regard to the substance, it is preferred that the substance is capable of accepting the energy or the electron from the compound to enhance the chemical species from the substance. Typical examples of such substance are substance which can act as electron-acceptors. Such electron-acceptors have at least one electron-accepting group such as cyano group, amide group, imide group, carbonyl group, trifluoromethyl group and onium group (e.g., ammonium group and sulfonium group). Phenyl dibenzothionium nonafluorobutanesulfonate (PBpS-PFBS), N-hydroxynaphtalimide nonafluolobutanesulfonate (NHNI-PFBS) and α-(trifluoromethylsulfonyloximino)-phenylacetonitrile (Oxime) described below are examples of such substance. Those photoacid generators have sulfonium group, imido group and cyano group, respectively. With regard to the substance, it is preferred that the substance is capable of being converted into a reactive intermediate by accepting the electron from the compound.

With regard to the substance, it is preferred that the reactive intermediate is capable of generating the chemical species.

With regard to the substance, it is preferred that the reactive intermediate is an anion radical. Typically, such anion radical is generated by acceptance of electron by the substance. A reagent relating to an aspect hereof is characterized in that the reagent is capable of generating a compound in at least one of a composition including the reagent, a liquid containing the composition and a film of the composition; and the compound is capable of enhancing a first chemical species from at least one of the compound and a substance by an interaction of the compound with the substance.

With regard to the reagent, it is preferred that the interaction is promoted by an exposure of the composition, the liquid and the film to at least one of a first electromagnetic ray and a first particle ray.

With regard to the reagent, it is preferred that the compound is formed through a reaction of the reagent with a second chemical species generated from the compound.

With regard to the reagent, it is preferred that the first chemical species is also generated from the reagent without any interaction with the compound; and the compound is formed by a reaction of the reagent with the first chemical species.

With regard to the reagent, it is preferred that the compound is capable of donating an electron to the reagent.

With regard to the reagent, it is preferred that the reagent is capable of generating the compound through processes triggered by supplying an energy to the film.

With regard to the reagent, it is preferred that a conjugation length of the compound is longer than a conjugation length of the reagent.

With regard to the reagent, it is preferred that: the reagent has at least two pi-electron systems; the compound has at least two pi-electron systems; and an electronic interaction between the at least two pi-electron systems in the compound is stronger than an electronic interaction between the at least two pi-electron systems in the reagent.

A composition relating to an aspect hereof includes the aforementioned substance and the compound.

A composition relating to an aspect hereof includes the aforementioned substance and a reagent capable of generating the compound.

With regard to the composition, it is preferred that the substance is a photoacid generator (PAG).

With regard to the composition, it is preferred that the composition further includes a polymer. Such polymer may react with the chemical species.

A polymer relating to an aspect hereof includes a first moiety capable of interacting with a substance; and a second moiety which is to react with a chemical species.

With regard to the polymer, it is preferred that the first moiety donates an energy or an electron to the substance or accepts an energy or an electron from the substance.

With regard to the polymer, it is preferred that the polymer further includes a third moiety from which the chemical species is to be generated.

With regard to such composition, it is preferred that the composition is characterized by that the composition is used for formation of an interlayer insulating film of a device.

With regard to such composition, it is preferred that the interlayer insulating film is formed of at least one portion of the composition.

A polymer relating to an aspect hereof includes: a third moiety capable of being converted into a fourth moiety capable of interacting with a substance; and a fifth moiety which is to react with a chemical species.

With regard to such polymer, it is preferred that the third moiety is converted into the fourth moiety by reacting with the chemical species.

A composition relating to an aspect hereof includes the aforementioned reagent; and the aforementioned substance.

A method for manufacturing a device relating to an aspect hereof is characterized by that the method being carried out by using the aforementioned composition.

A method for manufacturing a device relating to an aspect hereof includes: applying a liquid containing the aforementioned composition to a member such that a coating film including the composition is formed on the member; and exposing the coating film to at least one of a first electromagnetic ray and a first particle ray such that a first portion of the coating film is exposed to the at least one of the first electromagnetic ray and the first particle ray while a second portion of the coating film is not exposed to the at least one of the first electromagnetic ray and the first particle ray.

With regard to such method, it is preferred that the method further includes: removing the first portion.

With regard to such method, it is preferred that the method further includes: etching the member such that a third portion of the member on which the first portion has been present is etched.

With regard to such method, it is preferred that the electromagnetic ray is a light of a wavelength ranges from 300 nm to 400 nm.

With regard to such method, it is preferred that a contact hole is formed by the removing of the first portion.

With regard to such method, it is preferred that the method further includes: forming an active layer before the applying of the liquid containing the composition is carried out; and connecting the active layer to an electrode by disposing a conductive material in the contact hole.

A method for manufacturing a device relating to an aspect hereof is characterized by that the method being carried out by using the aforementioned composition.

A method for manufacturing a device relating to an aspect hereof includes: applying a liquid containing the aforementioned composition to a member such that a coating film including the composition is formed on the member; and exposing the coating film to at least one of the first electromagnetic ray and the first particle ray such that a first portion of the coating film is exposed to the at least one of the first electromagnetic ray and the first particle ray while a second portion of the coating film is not exposed to the at least one of the first electromagnetic ray and the first particle ray.

With regard to such method, it is preferred that such method further includes: removing the first portion.

With regard to such method, it is preferred that such method further includes: etching the member such that a third portion of the member on which the first portion has been present is etched.

With regard to such method, it is preferred that the first electromagnetic ray is a light of a wavelength ranges from 300 nm to 400 nm.

With regard to such method, it is preferred that a contact hole is formed by the removing of the first portion.

With regard to such method, it is preferred that the method further includes: forming an active layer before the applying of the liquid containing the composition is carried out; and connecting the active layer to an electrode by disposing a conductive material at least in the contact hole.

With regard to such method, it is preferred that the compound is not excited by the exposing of the coating film.

With regard to such method, it is preferred that the compound does not absorb the first electromagnetic ray.

With regard to such composition, it is preferred that the compound does not absorb the first electromagnetic ray.

With regard to such composition, it is preferred that the compound is not excited by the first electromagnetic ray.

A compound that assists generation of a chemical species such as acid and a composition are disclosed in the disclosure. Typically, such compound assists the generation of Brönsted acid or Brönsted base from a precursor. Furthermore, such compound can be applied to enhancement of the generation of Lewis acid or Lewis base.

Typically, such compound in its ground state or excited state donates energy or an electron to a precursor or accepts energy or an electron from a precursor to form a reactive intermediate or an excited state of the precursor which can easily generate a chemical species. Such compound can have existed in unchanged form until such compound interacts or reacts with the precursor. Alternatively, such compound can be generated from a reagent in situ before such compound interacts or reacts with the precursor. In that case, such compound can be generated in situ by a reaction of such reagent or an intermediate generated from such reagent with a chemical species. Alternatively, such compound can be generated by a unimolecular reaction of such reagent. It is preferred that such compound exhibits longer cutoff wavelength in its absorption spectrum than such reagent.

A compound relating to an aspect hereof has following characteristics: the compound absorbs a light of a wavelength longer than 220 nm; and the compound is capable of sensitizing a precursor to generate a chemical species from the precursor.

A reagent relating to an aspect hereof is capable of generating the compound mentioned above. Typically, supply of energy to a film containing such reagent generates the compound from the reagent. The compound has a longer conjugation length than the reagent. Such compound may be generated from a reagent by deprotection reaction of a protecting group of such compound.

A reagent relating to an aspect hereof has at least two pi-electron systems of the reagent. A compound having at least two pi-electron systems can be generated from such reagent. An electronic interaction between the at least two pi-electron systems in such compound is stronger than an electronic interaction between the at least two pi-electron systems in the reagent. Such reagent generates the compound through processes triggered by supplying energy to the film.

A compound relating to an aspect hereof is characterized by that the compound is capable of enhancing a generation of a chemical species from a substance.

A compound relating to an aspect hereof is characterized in that the compound is capable of donating an electron to a substance or accepting from a substance when the substance is excited; the substance is capable of generating a chemical species by accepting the electron from the compound or donating the electron to the compound.

With regard to any one of above compounds, it is preferred that: the compound has at least one aromatic group; and an electron-donating group. Examples of such aromatic groups are phenyl, naphthyl, anthryl, phenanthryl and pyrenyl. Such aromatic group can contain at least one hetero atom like thiophenyl, furyl, pyridyl, quinolyl, benzoquinolyl, carbazolyl, phenothiazinyl, benzofuryl, benzothiophenyl, dibenzofuryl, or dibenzothiophenyl. Such aromatic group can have at least one substituent. Examples of such electron-donating group are alkyl, hydroxy, alkoxy, aryloxy, amino, alkylamino, dialkylamino, alkylthio and arylthio groups.

With regard to any one of the above compounds, it is preferred that the compound has a multiple bond.

With regard to any one of above compounds, it is preferred that the multiple bond is any one of a carbon-oxygen double bond and carbon-carbon double bond.

Typical examples for such compound are aryl ethane having at least one aromatic group, aryl ketones such as alkoxy (or aryloxy) benzophenone, arylalkyl ketones and carbazoles. More concrete examples of such aryl are Compounds 1-3 described below while those of aryl ketone are the ketones generated from Reagents A and C-1 of Resin C by deprotection reaction of the acetal groups. For example, a composition relating to an aspect hereof contains at least one of such compound and reagent which is to form such compound, a precursor which is to form a chemical species, and a polymer that is to react with the chemical species. Such composition can be applied as a photoresist to fabrication of a device such as semiconductor device and electro-optical device. A typical example of such precursor is PAG while a typical example of such polymer is a polymer containing a substituent which is acid-dissociable. Typically, a set of processes for fabricating devices includes a step in which the composition is applied to a member to form a coating film and a step in which the coating film is exposed to a light of a wavelength longer than 200 nm.

In case that such compound is used as a constituent of a photoresist composition which can be applied to interlayer insulating films of display device such as LCD and OLED, it is preferred that such compound has very low absorption coefficient at wavelengths equal to or longer than 400 nm since the interlayer insulating films of such display device transmits visible lights or lights having wavelengths longer than 400 nm. It is more preferred that such compound exhibits little absorption at wavelengths longer than 400 nm.

A composition relating to an aspect hereof contains a precursor which is to generate a chemical species and at least one of such compound and such reagent mentioned above. Typical examples of such reagent have a shorter cutoff wavelength than such compound formed from such reagent. Even If a coating film formed by such composition is thick, a light penetrates deeply into the coating film and such compound can be generated even in the depths of the coating film.

Typically, such precursor is a PAG. The composition can further contain a polymer capable of reacting with the chemical species. Such composition can be used as a photoresist for formation of an interlayer insulating film of a device or constituent material for at least one portion of an interlayer insulating film of a device.

A polymer relating to an aspect hereof includes a first moiety capable of acting as a photosensitizing moiety and a second moiety which is to react with a chemical species. Such polymer may further include a third moiety which is to generate the chemical species.

A method for manufacturing a device relating to an aspect hereof is carried out by using such composition or such polymer mentioned above. The composition may contain at least one of such compound mentioned above and such reagent.

A method for manufacturing a device relating an aspect hereof includes the following steps: a first of application of a liquid containing the composition mentioned above to a member such that a coating film including the composition is formed on the member; a second step of an irradiation of the coating film with at least one of a electromagnetic ray and a particle ray such that a first portion of the coating film is irradiated with the at least one of the electromagnetic ray and the particle ray while a second portion of the coating film is not irradiated with the at least one of the electromagnetic ray and the particle ray; and a third step of removal of the first portion.

Such method can further include a step of etching of the member such that a third portion of the member on which the first portion has been present is etched.

In such method, a contact hole can be formed by the removal of the first portion. Such method can further include a step of formation of an active layer. The active layer can be connected to an electrode such as a pixel electrode by disposing a conductive material at least in the contact hole.

In such method, a light of a wavelength ranges from 350 nm to 400 nm can be used as the electromagnetic ray used for such method.

BRIEF DESCRIPTION OF THE DRAWINGS

In the drawings, which illustrate what is currently considered to be the best mode for carrying out several aspects of the disclosure.

DETAILED DESCRIPTION

Experimental Procedures

Figure 1:
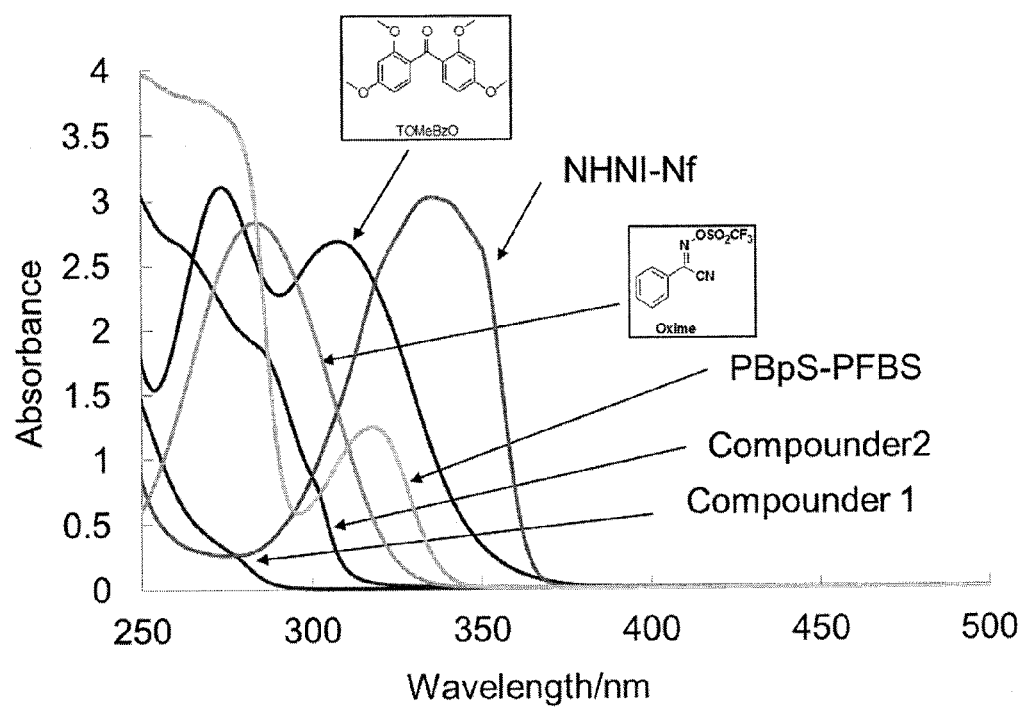
FIG. 1 shows absorption spectra of compounds relating to an aspect hereof.

Synthesis of 2-isopropenyl-1, 3, 5-trimethoxy-benzene. (Compound 1)

2.00 g of 2, 4, 6-trimethoxyacetophenone and 3.74 g of methyltriphenyphosphonium bromide are added to 20 g of tetrahydrofuran. 2.13 g of potassium tert-butoxide is added to the tetrahydrofuran mixture containing 2, 4, 6-trimethoxy-acetophenone and methyltriphenyphosphonium bromide. The mixture is stirred at 60 degrees Celsius for 2 hours and the mixture is filtrated. Afterwards, tetrahydrofuran is distilled away and 20 g of cyclohexane is added to the residue. The cyclohexane mixture is stirred for 10 minutes and a deposit is filtrated and the filtrate is collected. Thereafter, cyclohexane is distilled away, and the resultant is purified by silica gel column chromatography (ethyl acetate:hexane=10:90). Thereby 1.62 g of 2-isopropenyl-1, 3, 5-trimethoxy-benzene is obtained.

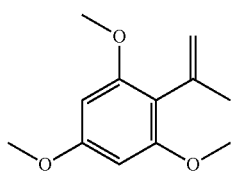

Compound 1

Synthesis of 2,2',4,4'-tetramethoxybenzophenone 2.00 g of 2, 2', 4, 4'-tetrahydroxybenzophenone, 3.68 g of dimethyl sulfate and 4.03 g of potassium carbonate are dissolved in 12.0 g of acetone. The mixture is stirred at reflux temperature for 8 hours. Since then, the mixture is cooled to 25 degrees Celsius and it is further stirred for 10 minutes after addition of 60.0 g of water and a deposit is filtrated. Then the deposit is dissolved in 20.0 g ethyl acetate and the organic phase is washed with water. Thereafter, ethyl acetate is distilled away, and the resultant is purified by recrystallization using 15.0 g of ethanol. Thereby 1.40 g of 2, 2', 4, 4'-tetramethoxybenzophenone is obtained.

Synthesis of 1,1-bis-(2,4-dimethoxyphenyl)-ethylene (Compound 2)

Synthesis of 1,1-bis-(2,4-dimethoxyphenyl)-ethylene as a target substance is synthesized and obtained according to the synthesis of Compound 1 mentioned above, except for using 2, 2', 4, 4'-tetramethoxybenzophenone instead of 2, 4, 6-trimethoxyacetophenone for the synthesis of Compound 1.

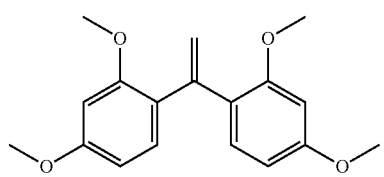

Compound 2

Synthesis of 3-(2, 4, 6-trimethoxy-phenyl)-but-2-en-1-ol 4.00 g of 2, 4, 6-trimethoxyacetophenone and 8.10 g of (2-hydroxyethyl)triphenyphosphonium bromide are added to 40 g of tetrahydrofuran. 3.80 g of 40% aqueous sodium hydroxide is added to the tetrahydrofuran mixture containing 2, 4, 6-trimethoxyaetophenone and (2-hydroxyethyl)triphenyphosphonium bromide. The mixture is stirred at 60 degrees Celsius for 4 hours and the mixture is filtrated. Afterwards, tetrahydrofuran is distilled away and 40 g of cyclohexane is added to the residue. The cyclohexane mixture is stirred for 10 minutes and a deposit is filtrated and the filtrate is collected. Thereafter, cyclohexane is distilled away, and the resultant is purified by silica gel column chromatography (ethyl acetate:hexane=10:90). Thereby 3.49 g of 3-(2, 4, 6-Trimethoxy-phenyl)-but-2-en-1-ol is obtained.

Synthesis of 2-methyl-acrylic acid 3-(2, 4, 6-trimethoxy-phenyl)-but-2-enyl ester (Compound 3)

3.00 g of 3-(2, 4, 6-trimethoxy-phenyl)-but-2-en-1-ol and 2.12 g of methacrylic anhydride are dissolved in 21 g of tetrahydrofuran. 1.52 g of triethylamine dissolved in 4.55 g of tetrahydrofuran is added dropwise to the tetrahydrofuran solution containing 3-(2, 4, 6-trimethoxy-phenyl)-but-2-en-1-ol over 10 minutes. After that the mixture is stirred at 25 degrees Celsius for 3 hours. Since then, the mixture is further stirred after addition of water. Then extracted with 60 g ethyl acetate and the organic phase is washed with water. Thereafter, ethyl acetate is distilled away, and the residue is purified by silica gel column chromatography (ethyl acetate:hexane=1:9). Thereby 3.04 g of 2-methyl-acrylic acid 3-(2, 4, 6-trimethoxy-phenyl)-but-2-enyl ester is obtained.

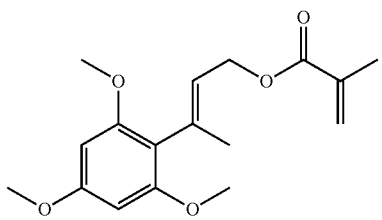

Compound 3

Synthesis of -(2,4-dimethoxyphenyl)-dimethoxymethane 1.4 g of 2,2',4,4'-tetramethoxybenzophenone is dissolved in 27.8 g of thionyl chloride. The mixture is stirred at reflux temperature for 5 hours. Since then, thionyl chloride is distilled away and the resultant is dissolved in 15 g of toluene. Then the prepared solution is added dropwise over 1 hour to 30.1 g of methanol solution containing 5.0 g of sodium methoxide at 5 degrees Celsius. The addition is completed. Then the mixture is warmed up to 25 degrees Celsius with stirring for 2 hours. Then, the mixture is further stirred after an addition of 50 g of pure water. Then methanol is distilled away, and the resultant is extracted by 35 g of toluene and the organic phase is washed with water. Thereafter, toluene is distilled away. Thereby 3.87 g of crude bis-(2,4-dimethoxyphenyl)-dimethoxymethane is obtained as an oil.

Synthesis of 2,2-bis-(2,4-dimethoxyphenyl)-1,3-dioxolane (Reagent A)

3.8 g of crude bis-(2,4-dimethoxyphenyl)-dimethoxymethane, 0.03 g of compher sulfonic acid and 2.03 g of ethyleneglycol are dissolved in 5.7 g of tetrahydrofuran. The mixture is stirred at 25 degrees Celsius for 72 hours. Since then, the organic solvents are distilled away and the resultant is dissolved in 11 g of dichloromethane. Then, the mixture is further stirred after addition of 5% aqueous solution of sodium carbonate and the organic phase is washed with 5% aqueous solution of sodium carbonate and water. Thereafter, dichloromethane is distilled away, and the residue is purified by silica gel column chromatography (ethyl acetate:hexane:triethylamine=10:90:0.01). Thereby 2.5 g of 2,2-bis-(2,4-dimethoxyphenyl)-1,3-dioxolane (Reagent A) is obtained.

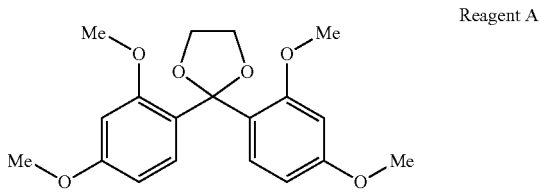 [SMILES: COc1ccc(C2(c3ccc(OC)cc3OC)OCCO2)c(OC)c1]

Reagent A

Synthesis of 2,4-dimethoxy-4'-(2-vinyloxy-ethoxy)-benzophenone 2.00 g of 2,4-dimethoxy-4'-hydroxybenzophenone, 2.48 g of 2-chloroethyl vinyl ether and 3.21 g of potassium carbonate are dissolved in 12.0 g of dimethyl formamide. The mixture is stirred at 110 degrees Celsius for 15 hours. Since then, the mixture is cooled to 25 degrees Celsius and it is further stirred after addition of 60.0 g of water. Then extracted with 24.0 g of toluene and the organic phase is washed with water. Thereafter, toluene is distilled away. Thereby 3.59 g of 2,4-dimethoxy-4'-(2-vinyloxy-ethoxy)-benzophenone is obtained.

Synthesis of 2,4-dimethoxy-4'-(2-hydroxy-ethoxy)-benzophenone 3.59 g of 2,4-dimethoxy-4'-(2-vinyloxy-ethoxy)-benzophenone, 0.28 g of pyridinium p-toluenesulfonate and 2.1 g of water are dissolved in 18.0 g of acetone. The mixture is stirred at 35 degrees Celsius for 12 hours. Since then, the mixture is further stirred after addition of 3% aqueous solution of sodium carbonate. Then extracted with 28.0 g ethyl acetate and the organic phase is washed with water. Thereafter, ethyl acetate is distilled away. Thereby 3.04 g of 2,4-dimethoxy-4'-(2-hydroxy-ethoxy)-benzophenone is obtained.

Synthesis of 2, 4-dimethoxy-4'-(2-methacryloxy-ethyl)-benzophenone 3.0 g of 2, 4-dimethoxy-4'-(2-hydroxy-ethoxy)-benzophenone and 1.7 g of methacrylic anhydride are dissolved in 21 g of tetrahydrofuran. 1.2 g of triethylamine dissolved in 3.6 g of tetrahydrofuran is added dropwise to the tetrahydrofuran solution containing 2, 4-dimethoxy-4'-(2-hydroxy-ethoxy)-benzophenone over 10 minutes. After that the mixture is stirred at 25 degrees Celsius for 3 hours. Since then, the mixture is further stirred after addition of water. Then extracted with 30 g of ethyl acetate and the organic phase is washed with water. Thereafter, ethyl acetate is distilled away, and the residue is purified by silica gel column chromatography (ethyl acetate:hexane=1:9). Thereby 2.72 g of 2, 4-dimethoxy-4'-(2-methacryloxy-ethyl)-benzophenone is obtained.

Synthesis of 2, 4-dimethoxy-4'-(2-acetoxy-ethoxy)-benzophenone

Synthesis of 2, 4-dimethoxy-4'-(2-acetoxy-ethoxy)-benzophenone as a target substance is synthesized and obtained according to the synthesis of Reagent 3 mentioned above, except for using acetic anhydride instead of methacrylic anhydride for the synthesis of Reagent 3.

Synthesis of (2, 4-dimethoxyphenyl)-[4'-(2-hydroxy-ethoxy)-phenyl]-dimethoxymethane)

Synthesis of (2, 4-dimethoxyphenyl)-[4'-(2-hydroxy-ethoxy)-phenyl]-dimethoxymethane) as a target substance is synthesized and obtained according to the synthesis of bis-(2,4-dimethoxyphenyl)-dimethoxymethane mentioned above, except for using 2, 4-dimethoxy-4'-(2-acetoxy-ethoxy)-benzophenone instead of 2,2',4,4'-tetramethoxybenzophenone for the synthesis of bis-(2,4-dimethoxyphenyl)-dimethoxymethane.

Synthesis of 2-(2, 4-dimethoxyphenyl)-2-[4'-(2-hydroxy-ethoxy)-phenyl]-1,3-dioxolane Synthesis of 2-(2, 4-dimethoxyphenyl)-2-[4'-(2-hydroxy-ethoxy)-phenyl]-1,3-dioxolane as a target substance is synthesized and obtained according to the synthesis of the Reagent A mentioned above, except for using (2, 4-dimethoxyphenyl)-[4'-(2-hydroxy-ethoxy)-phenyl]-dimethoxymethane instead of bis-(2,4-dimethoxyphenyl)-dimethoxymethane for the synthesis of Reagent A.

Synthesis of 2-(2, 4-dimethoxyphenyl)-2-[4'-(2-methacyloxy-ethoxy)-phenyl]-1,3-dioxolane (Reagent B)

Synthesis of 2-(2, 4-dimethoxyphenyl)-2-[4'-(2-methacyloxy-ethoxy)-phenyl]-1,3-dioxolane as a target substance is synthesized and obtained according to the synthesis of the Compound 3 mentioned above, except for using (2, 4-dimethoxyphenyl)-[4'-(2-hydroxy-ethoxy)-phenyl]-dimethoxymethane instead of 3-(2, 4, 6-trimethoxy-phenyl)-but-2-en-1-ol for the synthesis of Compound 3.

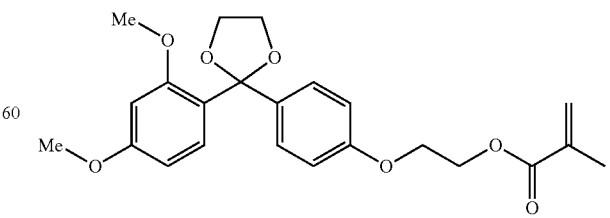

Reagent B

A solution containing 5.0 g of α-methacryloyloxy-γ-Butyrolactone, 6.03 g of 2-methyladamantane-2-methacrylate, and 4.34 g of 3-hydroxyadamantane-1-methacrylate, 0.51 g of dimethyl-2,2'-azobis(2-methylpropionate), and 26.1 g of tetrahydrofuran is prepared. The prepared solution is added for 4 hours to 20.0 g of tetrahydrofuran placed in flask with stirring and boiling. After the addition of the prepared solution, the mixture is heated to reflux for 2 hours and cooled to room temperature. Addition of the mixture by drops to a mixed liquid containing 160 g of hexane and 18 g of tetrahydrofuran with vigorously stirring precipitates the copolymer. The copolymer is isolated by filtration. Purification of the copolymer is carried out by vacuum drying following twice washings by 70 g of hexane, and thereby 8.5 g of white powder of the copolymer (Resin A) is obtained.

Resin A

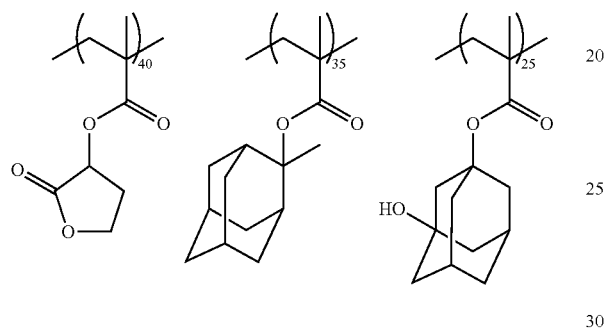

A solution containing 0.40 g of 2-methyl-acrylic acid 3-(2, 4, 6-trimethoxy-phenyl)-but-2-enyl ester (Compound 3), 9.44 g of α-methacryloyloxy-γ-butyrolactone, 7.07 g of 2-methyladamantane-2-methacrylate, 8.55 g of 3-hydroxyadamantane-1-methacrylate, 0.33 g of butyl mercaptane, 1.41 g of dimethyl-2,2'-azobis(2-methylpropionate) and 27.2 g of tetrahydrofuran is prepared. The prepared solution is added dropwise over 4 hours to 9.5 g of tetrahydrofuran placed in flask with stirring and boiling. After the addition of the prepared solution, the mixture is heated to reflux for 2 hours and cooled to room temperature. Addition of the mixture by drops to a mixed liquid containing 243 g of hexane and 27 g of tetrahydrofuran with vigorously stirring precipitates the copolymer. The copolymer is isolated by filtration. Purification of the copolymer is carried out by vacuum drying following twice washings by 100 g of hexane, and thereby 14.8 g of white powder of the copolymer (Resin B) is obtained.

Resin B

B-1

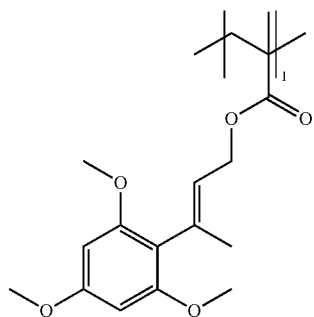

B-2

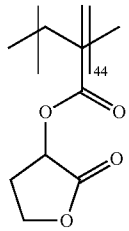

B-3

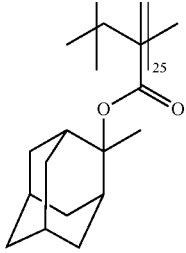

B-4

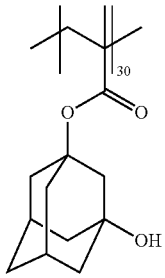

A solution containing 0.40 g of 2-(2, 4-dimethoxyphenyl)-2-[4'-(2-methacyloxy-ethoxy)-phenyl]-1,3-dioxolane (Reagent B), 7.6 g of α-methacryloyloxy-γ-butylolactone, 5.6 g of 2-methyladamantane-2-methacrylate, 6.8 g of 3-hydroxyadamantane-1-methacrylate, 0.27 g of butyl mercaptane, 1.13 g of dimethyl-2,2'-azobis(2-methylpropionate) and 22.2 g of tetrahydrofuran is prepared. The prepared solution is added dropwise over 4 hours to 7.6 g of tetrahydrofuran placed in flask with stirring and boiling under nitrogen atmosphere. After the addition of the prepared solution, the mixture is heated to reflux for 2 hours and cooled to room temperature. Addition of the mixture by drops to a mixed liquid containing 195 g of hexane and 21 g of tetrahydrofuran with vigorously stirring precipitates the copolymer. The copolymer is isolated by filtration. Purification of the copolymer is carried out by vacuum drying following twice washings by 40 g of hexane, and thereby 6.8 g of white powder of the copolymer (Resin C) is obtained.

Resin C

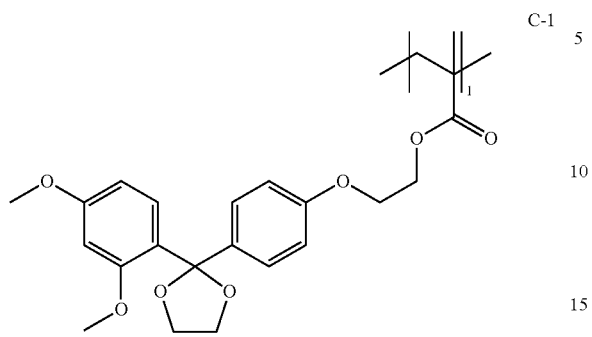
C-1

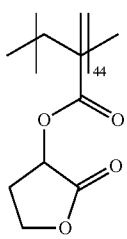
C-2

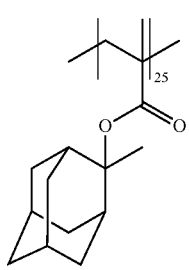
C-3

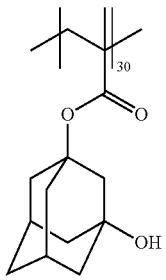
C-4

Preparation of Samples for Evaluation (the "Evaluation Samples")

Evaluation Samples 1-17 are prepared by dissolving in 2000 mg of cyclohexanone (i) 0.032 mmol of a PAG selected from a group of consisting of phenyl dibenzothionium nonafluorobutanesulfonate (PBpS-PFBS) and N-hydroxynaphtalimide nonafluolobutanesulfonate (NHNI-PFBS), (ii) 450 mg of a resin selected from a group consisting of Resins A, B and C, and (iii) 0.017 mmol of additive selected from a group consisting of Compounds and/or Reagents mentioned above, or (iv) 0 mmol of additive. And also Evaluation Samples 18 and 19 are prepared using 0.017 mmol of 2,4-diethylthioxanthen-9-one (DETX) as an additive. Table 1 shows detail of sample compositions.

TABLE 1

Evaluation Samples for evaluation for efficiencies of patterning

| | Resin | PAG | Additive (composition ratio) | UV-light |
|---|---|---|---|---|
| Evaluation Sample 1 | Resin A | PBpS-PFBS | — | UV-A |
| Evaluation Sample 2 | | | — | UV-B |
| Evaluation Sample 3 | | | Compound 1 [0.068 mmol] | UV-A |
| Evaluation Sample 4 | | | Compound 2 [0.068 mmol] | UV-A |
| Evaluation Sample 5 | | | Reagent A | UV-A |
| Evaluation Sample 6 | | | Reagent A (0.7) Compound 2 (0.3) | UV-A |
| Evaluation Sample 7 | | NHNI-PFBS | — | UV-B |
| Evaluation Sample 8 | | | Compound 1 | UV-B |
| Evaluation Sample 9 | | | Compound 1 [0.026 mmol] | UV-B |
| Evaluation Sample 10 | | | Compound 2 | UV-B |
| Evaluation Sample 11 | | | Reagent A (0.7) Compound 2 (0.3) | UV-B |
| Evaluation Sample 12 | Resin B | PBpS-PFBS | — | UV-A |
| Evaluation Sample 13 | | NHNI-PFBS | — | UV-B |
| Evaluation Sample 14 | Resin C | PBpS-PFBS | — | UV-A |
| Evaluation Sample 15 | | | Compound 2 (0.3) | UV-A |
| Evaluation Sample 16 | | NHNI-PFBS | — | UV-B |
| Evaluation Sample 17 | | | Compound 2 (0.3) | UV-B |
| Evaluation Sample 18 | Resin A | PBpS-PFBS | DETX | UV-A |
| Evaluation Sample 19 | | NHNI-PFBS | DETX | UV-B |

Before applying an Evaluation Sample to a Si wafer, hexamethyldisilazane (HMDS, Tokyo Chemical Industry) is spin-coated at 2000 rpm for 20 seconds on the surface of a Si wafer and baked at 110 degrees Celsius for 1 minute. Then, an Evaluation Sample is spin-coated on the surface Si wafers which has been treated with HMDS at 2000 rpm for 20 seconds to form a coating film. The prebake of the coating film is performed at 110 degrees Celsius for 60 seconds. Then the coating film of the Evaluation Sample is exposed to any one of two kinds of ultraviolet (UV) lights. One is a UV light of which wavelength ranges from 320 nm to 360 nm outputted from FL-6BLB by Toshiba (UV-A). The other is a UV light of which wavelengths range from 350 nm to 380 nm (UV-B) output from FL-6BL by Hitachi (UV-B). After that the UV light exposure, a post-exposure-bake (PEB) is carried out at 110 degrees Celsius for 60 seconds. The coating film is developed with NMD-3 (tetramethyl ammonium hydroxide 2.38%, Tokyo Ohka Kogyo) for 20 seconds at 25 degrees Celsius and rinsed with deionized water for 10 seconds. The thickness of the coating film measured using film thickness measurement tool is approximately 500 nm.

An Evaluation Sample is measured by ultraviolet-visible spectroscopy to evaluate the transmittance of films at 400 nm before UV light irradiation. Thereafter, a sensitivity ($E_0$ sensitivity) is evaluated by measuring the dose size to form a pattern constituted by 100 μm lines where the thickness of the coating film is not zero and 100 μm spaces where the thickness of the coating film is zero using UV exposure system, and dose for $E_0$ sensitivity is calculated by means of a measurement of illuminance of UV source by 365 nm illuminometer (USHIO UIT-150, UVD-S365).

Table 2 shows the dose sizes corresponding to $E_0$ sensitivities measured for the Evaluation Samples 1 to 17. Formation of acid by an irradiation by UV exposure is not observed for Evaluation Samples 1. A tiny amount of acid is generated for Evaluation Sample 5. The $E_0$ sensitivities are high for Evaluation Samples containing Compound 2, which has higher electron-donating ability than Compound 1.

With regard to Evaluation Samples containing NHNI-PFBS as a PAG, higher sensitivities are observed for Evaluations Samples 8, 9, 10 and 11, each of which contains Compound 1 or Compound 2 acting as an electron donor, compared to Evaluation Sample 7, which does not contain such electron donor. This indicates that neutral-type PAG such as NHNI-PFBS can act as a photosensitizer. More concretely, such PAG can act as photosensitizer which accepts an electron from an electron donor.

With regard to Evaluation Samples, which contain PBpS-PFBS as a PAG and are irradiated with UV-A, higher sensitivities are observed for Evaluations Samples 3 and 4, each of which contains Compound 1 or Compound 2 acting as an electron donor, compared to Evaluation Sample 1 which does not contain such electron donor. This indicates that organic-salt-type PAG such as PBpS-PFBS can act as a photosensitizer. More concretely, such PAG can act as a photosensitizer which accepts an electron from an electron donor.

With regard to Evaluation Samples 18 and 19, each of which contains PAG and DETX, it is considered that PAG and DETX are an electron acceptor and electron donor, respectively.

The above results indicate that utilization of photosensitizing or electron-transfer reaction can enhance efficiency of formation of a chemical species such as acid.

Resin B shows higher sensitivity than Compound 1 although the electron-donating ability of B-1 moiety included in Resin B is similar to that of Compound 1. An incorporation B-1 moieties acting as electron-donors into polymer enables homogeneous dispersion of the electron-donors, which improves of acid generation efficiency.

Each of Evaluation Samples 6, 11, 15 and 17 contains a moiety or reagent which is protected by a protecting group such as alkoxy acetal and to form a corresponding electron donor or photosensitizer through a deprotection reaction with acid.

Reagent A contained in each of Evaluation Samples 6 and 11 reacts with acid to form in situ a corresponding ketone which acts as a photosensitizer for a UV light or an electron donor while the moiety C-1 of Resin C contained in each of Evaluation Samples 15 and 17 reacts with acid to form in situ a corresponding moiety containing a ketone group which act as a photosensitizer for a UV light or electron donor.

Reagent A, the ketone compound, the moiety C-1 and the ketone-group moiety have plural pi-electron systems. An electronic interaction between at least two pi-electron systems of the plural pi-electron systems of such Reagent A is weaker than that of the ketone compound. An electronic interaction between at least two pi-electron systems of the plural pi-electron systems of the moiety C-1 is weaker than that of the ketone-group moiety. The two pi-electron systems of such ketone compound or ketone moiety interact mutually through pi electrons or unshared electron pair of the carbonyl group. In other words, such products have pi-electron systems interacting more strongly each other compared to such precursor. Due to such electronic interaction, such products can absorb a longer-wavelength light compared to such precursors such as Reagent A and the moiety C-1.

The conjugation length of such precursors is shorter than that of such products. In such products, conjugation length is longer because of the stronger electronic interaction of the two pi-electron systems through pi electrons or unshared electron pair of carbonyl group.

Each of Evaluation Samples 11 and 17 contain a photosensitizer which accepts an electron such as NHNI-PFBS in addition to a precursor of photosensitizer or electron donor. In other words, each of Evaluation Samples 11 and 17 contains both two types of photosensitizers which are a photosensitizer accepting an electron and a photosensitizer donating an electron. Such plural types of photosensitization can additionally enhance the efficiency of formation of a chemical species such as acid.

Addition of such precursor such as Reagent A and the moiety C-1 provides a composition containing such precursor and PAG and with preservation stability and a film formed from such composition with the long-term reliability because such precursor is hard to absorbs a longer-wavelength UV light due to a weaker electronic interaction between plural pi-electron systems. Such composition is especially useful for constituent material for film such as insulating film or planarizing film of a display device because suppression of formation of acid can be attained during normal operation of the display device.

TABLE 2

The doses for $E_0$ by UV exposure for the Evaluation Samples.

| | Dose for $E_0$ Dose at 365 nm [mJ/cm$^2$] | Transmittance at 400 nm |
|---|---|---|
| Evaluation Sample 1 | 900 | 99.9 |
| Evaluation Sample 2 | >1500 | 99.9 |
| Evaluation Sample 3 | 820 | 99.9 |
| Evaluation Sample 4 | 525 | 99.9 |
| Evaluation Sample 5 | 320 | 99.8 |
| Evaluation Sample 6 | 290 | 99.8 |
| Evaluation Sample 7 | 210 | 99.8 |
| Evaluation Sample 8 | 45 | 99.9 |
| Evaluation Sample 9 | 30 | 99.8 |
| Evaluation Sample 10 | 30 | 99.8 |
| Evaluation Sample 11 | 35 | 99.8 |
| Evaluation Sample 12 | 870 | 99.9 |
| Evaluation Sample 13 | 42 | 99.8 |
| Evaluation Sample 14 | 300 | 99.8 |
| Evaluation Sample 15 | 275 | 99.8 |
| Evaluation Sample 16 | 50 | 99.8 |
| Evaluation Sample 17 | 30 | 99.8 |
| Evaluation Sample 18 | 130 | 87.6 |
| Evaluation Sample 19 | 30 | 87.3 |

FIG. 1 shows absorption spectra of Compound 1, Compound 2, PBpS-PFBS, NHNI-PFBS, Oxime and TOMeBzO in a solution. Compound 1 and Compound 2 exhibit little absorption at wavelength longer than 350 nm. Therefore, Compound 1 and Compound 2 are especially suitable for electron donors enhancing generation of acid from PAG contained in a photoresist applicable to fabrication of an interlayer insulating film of display device such as liquid crystal device and organic electroluminescent device. Compound 1 or Compound 2 are also useful for a constituent of material forming an interlayer insulating film of such display device because Compound 1 and Compound 2 hardly absorb a light of a wavelength longer than 400 nm, which is desired to pass through the interlayer insulating film. Visible lights usually pass through interlayer insulating films of display devices for performing display. If a substance which can acts as a photosensitizer or PAG by absorbing a visible light remains in an interlayer insulating film, acid is generated even during normal operations and deteriorates display device.

TOMeBzO can be formed from Reagent A by reaction with acid and act as a photosensitizer which donates an electron to PAG.

α-(trifluoromethylsulfonyloximino)-phenylacetonitrile (Oxime) can act as a PAG and a photosensitizer which accepts an electron. The efficiency of formation of acid from Oxime can be improved by an electron-transfer reaction involved with Oxime similar to NHNI-PFBS.

solution may be equal to or greater than 2. A preferable $Ab_{365}/Ab_{400}$ in a solution is equal to or greater than 4. A more preferable $Ab_{365}/Ab_{400}$ in a solution is equal to or greater than 10. A preferable $Ab_{365}/Ab_{400}$ in a film is equal to or greater than 50. A more preferable $Ab_{365}/Ab_{400}$ in a film is equal to or greater than 100.

Figure 2:
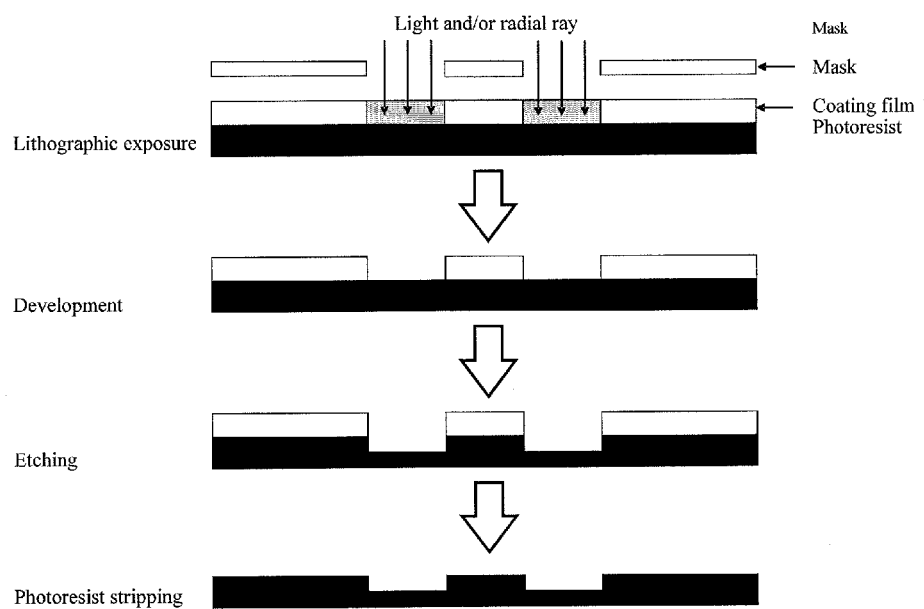
FIG. 2 shows fabrication processes of a device such as integrated circuit (IC) using a photoresist relating to an aspect hereof.

FIG. 2 shows fabrication processes of a device such as integrated circuit (IC) using Evaluation Sample 9 as a composition for a chemically amplified resist (CAR).

A silicon wafer is provided. The surface of silicon wafer is oxidized by heating the silicon wafer in the presence of oxygen gas.

A liquid containing Evaluation Sample 9 is applied to the surface of the Si wafer by spin coating to form a coating film. The coating film is prebaked.

An irradiation of the coating film with a light of a wavelength equal to or longer 220 nm through a mask is carried out after prebake of the Si wafer. A typical light source for the irradiation of the coating film is i-line or g-line.

NHNI-PFBS enhance generation of acid by acting as a photosensitizer which accepts an electron from Compound 1 in addition to PAG. The deprotection reaction of resin A is induced by acid generated by the photosensitizing reaction.

The coating film and the silicon wafer are exposed to the light. After that, the remaining film is removed.

An electronic device such as integrated circuit is fabricated utilizing the processes shown in FIG. 2. The deterio-

TABLE 3

Absorption characteristics of materials relating to an aspect hereof.

| | Absorbance (365 nm) | Absorbance (400 nm) | Concentration (mM) | Concentration (mol/L) | Absorption Coefficient ($\epsilon$ at 365 nm) | Absorption Coefficient ($\epsilon$ at 400 nm) | ($\epsilon$ at 365 nm)/ ($\epsilon$ at 400 nm) |
|---|---|---|---|---|---|---|---|
| TOMeBzO | 0.08692 | 0.00702 | 0.25 | 0.00025 | 347.68 | 28.08 | 12.38 |
| Compounder 2 | 0.0044 | 0.00212 | 0.25 | 0.00025 | 17.60 | 8.48 | 2.08 |
| Compounder 1 | 0.00055 | 0.00012 | 0.25 | 0.00025 | 2.20 | 0.48 | 4.58 |
| NHNI-PFBS | 0.18446 | 0.0047 | 0.25 | 0.00025 | 737.84 | 18.80 | 39.25 |
| Oxime | 0.00425 | 0.00241 | 0.25 | 0.00025 | 17.00 | 9.64 | 1.76 |
| PBpS-PFBS | 0.00068 | 0.00027 | 0.25 | 0.00025 | 2.72 | 1.08 | 2.52 |

Typically, the molar absorption coefficient at 400 nm of PAG relating to an aspect hereof in a solution is equal to or lower than 400. It is preferred that the molar absorption coefficient is equal to or lower than 200. More preferably, the molar absorption coefficient is equal to or lower than 100. The molar absorption coefficients of Compound 1 and Compound 2 are equal to or lower than 50.

A typical ratio of absorbance of such PAGs at 365 nm ("$Ab_{365}$") to absorbance at 400 nm ("$Ab_{400}$") in a solution may be equal to or greater than 2. A preferable $Ab_{365}/Ab_{400}$ in a solution is equal to or greater than 4. A more preferable $Ab_{365}/Ab_{400}$ in a solution is equal to or greater than 10. A preferable $Ab_{365}/Ab_{400}$ in a film is equal to or greater than 50. A more preferable $Ab_{365}/Ab_{400}$ in a film is equal to or greater than 100.

Typically, the molar absorption coefficient at 400 nm of electron donor relating to an aspect hereof in a solution is equal to or lower than 400. It is preferred that the molar absorption coefficient is equal to or lower than 200. More preferably, the molar absorption coefficient is equal to or lower than 100. The molar absorption coefficients of Compound 1 and Compound 2 are equal to or lower than 50.

A typical ratio of absorbance of such electron donors at 365 nm ("$Ab_{365}$") to absorbance at 400 nm ("$Ab_{400}$") in a ration of the device due to the irradiation with a light is suppressed compared to existing photoresists since times for irradiation of the coating film can be shortened.

Figure 3A:
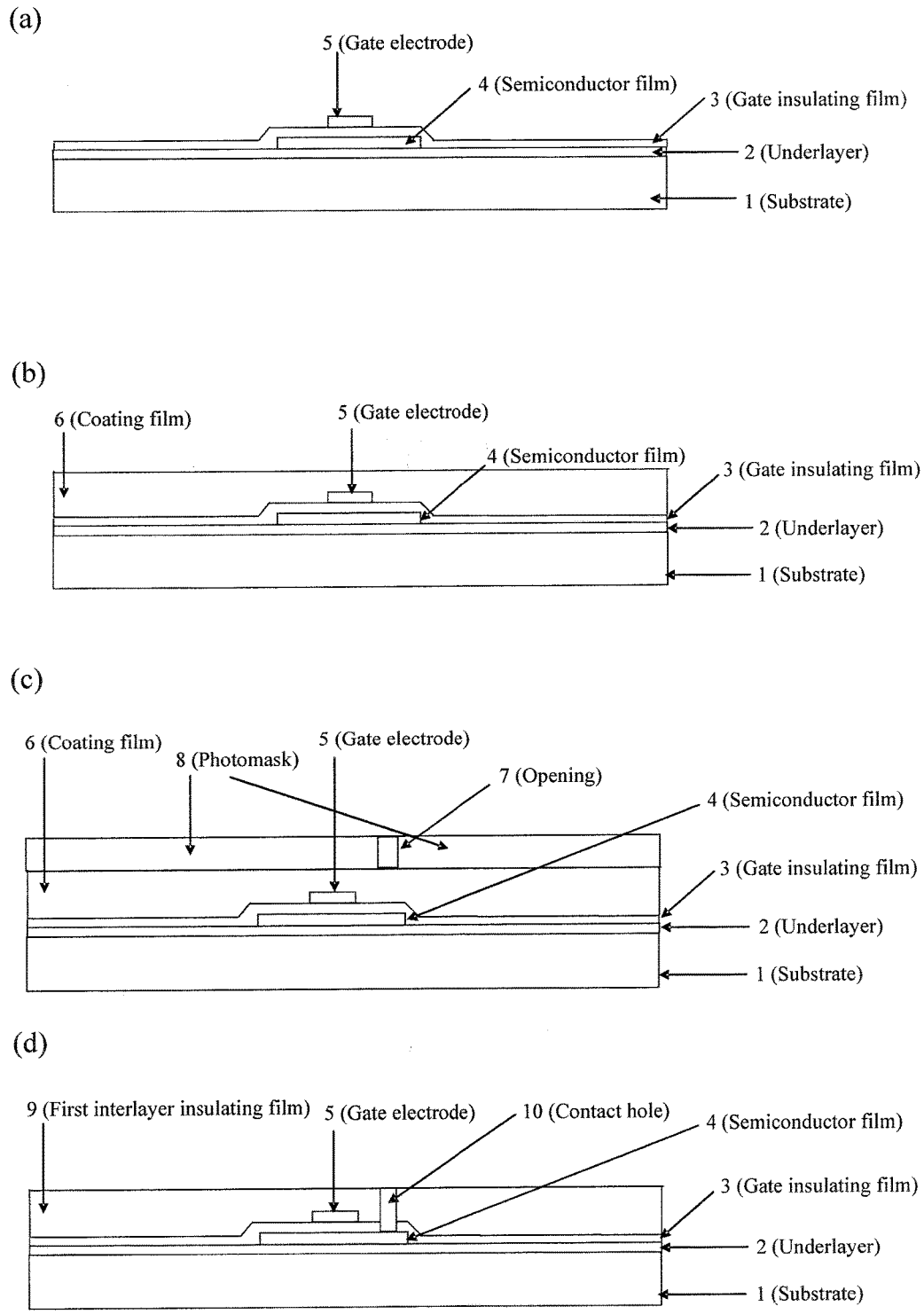
FIGS. 3A-3C show fabrication processes of a display device such as organic electroluminescent device (OLED) using a photoresist relating to an aspect hereof.
Figure 3B:
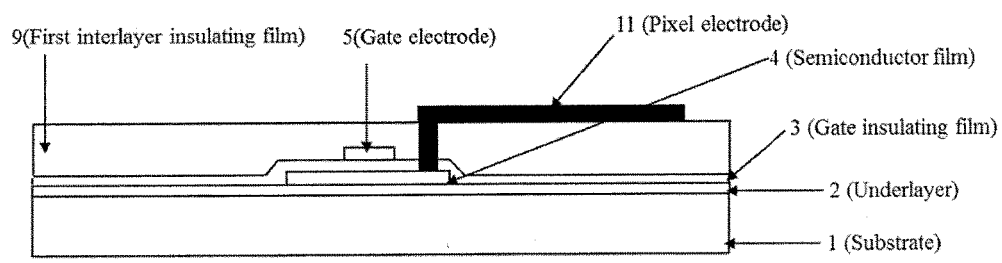
Figure 3B:
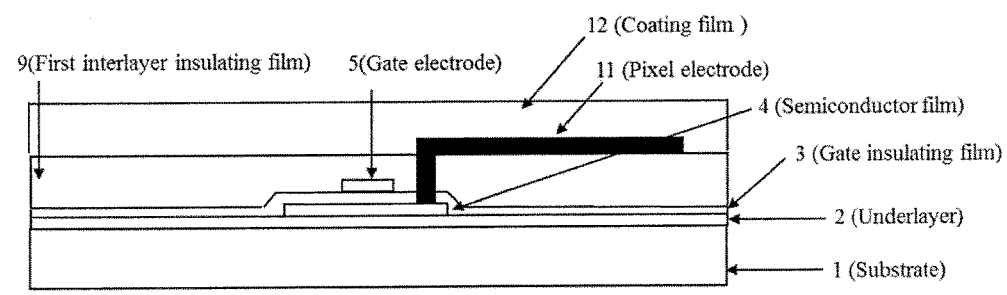
Figure 3C:
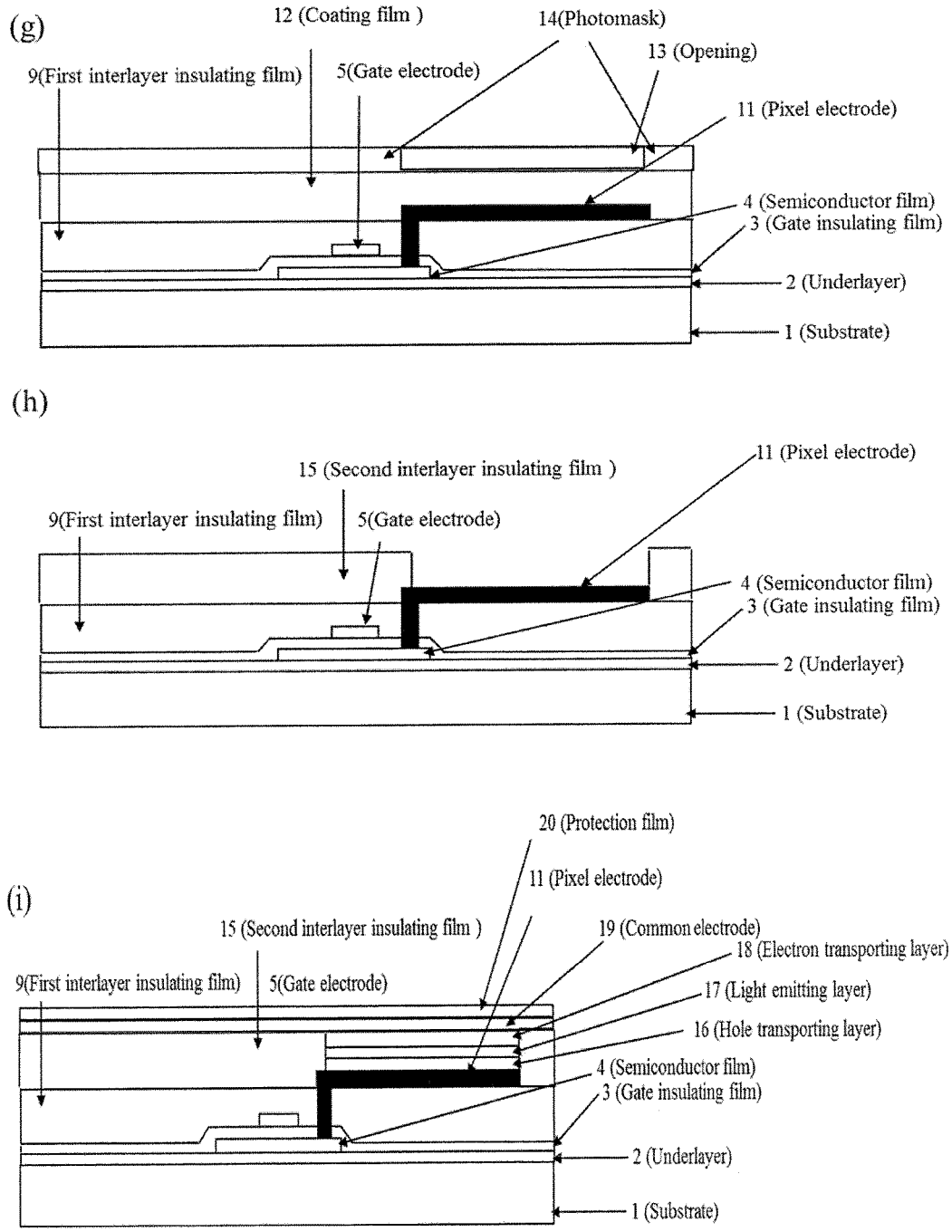

FIGS. 3A-3C show fabrication processes for active matrix-type organic electroluminescent device.

(a) Underlayer 2 is formed on a Substrate 1 such as glass substrate, quartz substrate and plastic substrate. Semiconductor film 4 which is formed by patterning is formed on Underlayer 2. Typically, Semiconductor film 4 is made of low-temperature polysilicon. Amorphous silicon or metal oxide can also be used as material for Semiconductor film 4. Gate insulating film 3 is formed such that Gate insulating film 3 covers Semiconductor film 4. Gate electrode 5 is formed over Gate insulating film 3 such that Gate electrode 5 and Semiconductor film 4 face each other across Gate insulating film 3.

(b) Coating film 6 is disposed by spin-coating of a composition containing Evaluation Sample 9 such that Coating film 6 covers Gate electrode 5 and Gate insulating film 3.

(c) Coating film 6 is irradiated with a light of which wavelength 365 nm through Photomask 8 after Coating film 6 is subjected to prebake treatment. Only a portion of Coating film 6 is exposed to a light passing through Opening 7.

(d) The exposed portion of Coating film 6 by the light is removed by development to form Contact hole 10. Coating film 6 is converted into First interlayer insulating film 9 by a heat treatment carried out at a temperature higher than 150 degrees centigrade following formation of Coating film 6.

(e) Pixel electrode 11 which is electrically connected to Semiconductor film 4 is formed. Typically, Pixel electrode 11 is made of Indium Tin Oxide (ITO) or magnesium-silver alloy.

(f) Coating film 12 is disposed by spin-coating process such that Coating film 12 covers Pixel electrode 11 and First interlayer insulating film 9.

(g) Coating film 12 is irradiated with a light of which wavelength 365 nm through Photomask 14 after Coating film 12 is subjected to prebake treatment. Only a portion of Coating film 12 is exposed to a light passing through Opening 13.

(h) The exposed portion of Coating film 12 by the light is removed by development. Coating film 12 is converted into Second interlayer insulating film 15 by a heat treatment carried out at a temperature higher than 150 degrees centigrade following removal of the exposed portion of Coating film 12.

(i) Hole transport layer 16, Light emitting layer 17 and Electron transporting layer 18 are formed by vacuum vapor deposition via mask in this order. Common electrode 19 is formed over Electron transporting layer 18 and Second interlayer insulating film 15. Protection film 20 is formed over Common electrode 19.

What is claimed is:

1. A composition comprising:
a first polymer including an acid-dissociable substituent that is to react with a generated acid;
a photoacid generator;
a second polymer including the following unit represented by Formula (B-1)

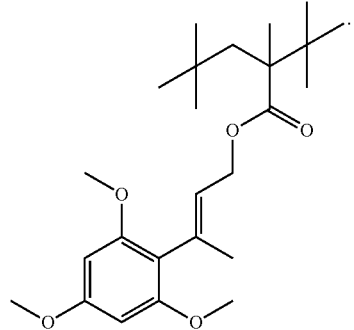

B-1

2. The composition of claim 1, wherein:
the first polymer and the second polymer are the same polymer, and the acid-dissociable substituent and the unit represented by Formula (B-1) are included in one polymer.

3. An interlayer insulating film of a device which includes a layer of the composition of claim 1.

* * * * *